US009295433B2

(12) United States Patent
Jackson et al.

(10) Patent No.: US 9,295,433 B2
(45) Date of Patent: *Mar. 29, 2016

(54) SYNCHRONIZED PATIENT ELEVATION AND POSITIONING APPARATUS FOR USE WITH PATIENT POSITIONING SUPPORT SYSTEMS (71) Applicant: Roger P. Jackson, Prairie Village, KS (US)

(72) Inventors: Roger P. Jackson, Prairie Village, KS (US); Lawrence E. Guerra, Mission, KS (US); Michael A. Herron, Overland Park, KS (US)

(73) Assignee: Roger P. Jackson, Prairie Village, KS (US)

( * ) Notice: Subject to any disclaimer, the term of this patent is extended or adjusted under 35 U.S.C. 154(b) by 94 days.

This patent is subject to a terminal disclaimer.

(21) Appl. No.: 13/955,642

(22) Filed: Jul. 31, 2013

(65) Prior Publication Data
US 2013/0312181 A1 Nov. 28, 2013

Related U.S. Application Data (63) Continuation-in-part of application No. 13/317,012, filed on Oct. 6, 2011, now Pat. No. 8,719,979, which is a continuation of application No. 12/460,702, filed on Jul. 23, 2009, now Pat. No. 8,060,960, and a (Continued)

(51) Int. Cl.
*A61G 13/04* (2006.01)
*A61B 6/04* (2006.01)
*A61G 7/008* (2006.01)

(Continued)

(52) U.S. Cl.
CPC ............ *A61B 6/0407* (2013.01); *A61G 7/001* (2013.01); *A61G 7/008* (2013.01); *A61G 13/0036* (2013.01); *A61G 13/04* (2013.01); *A61G 13/08* (2013.01); *A61G 7/012* (2013.01); *A61G 2013/0054* (2013.01);

(Continued)

(58) Field of Classification Search
CPC    A61G 13/04; A61G 7/001; A61G 2013/0054
USPC ..................... 5/607, 611, 612, 620
See application file for complete search history.

(56) References Cited

U.S. PATENT DOCUMENTS 1,098,477 A    6/1914    Cashman
1,171,713 A    2/1916    Gilkerson (Continued)

FOREIGN PATENT DOCUMENTS

EP    2226010 B1    6/2014
GB    569758    6/1945

(Continued)

OTHER PUBLICATIONS

Brochure of OSI on Modular Table System 90D, pp. 1-15, date of first publication: Unknow.

(Continued)

*Primary Examiner* — Michael Trettel
(74) *Attorney, Agent, or Firm* — Polsinelli PC (57) ABSTRACT An apparatus for transferring a supine patient to a prone position on a patient support structure, and for rotating such a prone patient between prone and supine positions without removing the patient from the patient support structure.

26 Claims, 6 Drawing Sheets

Related U.S. Application Data continuation of application No. 11/788,513, filed on Apr. 20, 2007, now Pat. No. 7,565,708, and a continuation-in-part of application No. 11/159,494, filed on Jun. 23, 2005, now Pat. No. 7,343,635, which is a continuation-in-part of application No. 11/062,775, filed on Feb. 22, 2005, now Pat. No. 7,152,261.

(60) Provisional application No. 61/742,167, filed on Aug. 3, 2012, provisional application No. 60/798,288, filed on May 5, 2006.

(51) Int. Cl.
*A61G 7/00* (2006.01)
*A61G 13/00* (2006.01)
*A61G 13/08* (2006.01)
*A61G 7/012* (2006.01)

(52) U.S. Cl.
CPC .... *A61G 2200/325* (2013.01); *A61G 2200/327* (2013.01); *A61G 2210/10* (2013.01)

(56) References Cited

U.S. PATENT DOCUMENTS

| | | | |
|---|---|---|---|
| 1,528,835 A | | 3/1925 | McCullough |
| 1,667,982 A | | 5/1928 | Pearson |
| 1,780,399 A | * | 11/1930 | Munson ............ 5/607 |
| 1,799,692 A | | 4/1931 | Knott |
| 1,938,006 A | | 12/1933 | Blanchard |
| 1,990,357 A | | 2/1935 | Ward |
| 2,188,592 A | | 1/1940 | Hosken et al. |
| 2,261,297 A | | 11/1941 | Frederick |
| 2,475,003 A | | 7/1949 | Black |
| 2,636,793 A | | 4/1953 | Meyer |
| 2,688,410 A | | 9/1954 | Nelson |
| 2,792,945 A | | 5/1957 | Brenny |
| 3,046,071 A | | 7/1962 | Shampaine et al. |
| 3,049,726 A | * | 8/1962 | Getz ............ 5/86.1 |
| 3,281,141 A | | 10/1966 | Smiley et al. |
| 3,584,321 A | | 6/1971 | Buchanan |
| 3,599,964 A | | 8/1971 | Magni |
| 3,766,384 A | | 10/1973 | Anderson |
| 3,814,414 A | | 6/1974 | Chapa |
| 3,832,742 A | | 9/1974 | Stryker |
| 3,988,790 A | | 11/1976 | Mracek et al. |
| 4,101,120 A | | 7/1978 | Seshima |
| 4,131,802 A | | 12/1978 | Braden et al. |
| 4,144,880 A | | 3/1979 | Daniels |
| 4,148,472 A | | 4/1979 | Rais et al. |
| 4,175,550 A | | 11/1979 | Leininger et al. |
| 4,186,917 A | | 2/1980 | Rais et al. |
| 4,227,269 A | | 10/1980 | Johnston |
| 4,230,100 A | | 10/1980 | Moon |
| 4,391,438 A | | 7/1983 | Heffington, Jr. |
| 4,474,364 A | | 10/1984 | Brendgord |
| 4,503,844 A | | 3/1985 | Siczek |
| 4,552,346 A | | 11/1985 | Schnelle et al. |
| 4,712,781 A | | 12/1987 | Watanabe |
| 4,718,077 A | | 1/1988 | Moore et al. |
| 4,763,643 A | | 8/1988 | Vrzalik |
| 4,771,785 A | | 9/1988 | Duer |
| 4,872,657 A | | 10/1989 | Lussi |
| 4,887,325 A | | 12/1989 | Tesch |
| 4,937,901 A | | 7/1990 | Brennan |
| 4,944,500 A | | 7/1990 | Mueller et al. |
| 4,953,245 A | | 9/1990 | Jung |
| 4,970,737 A | | 11/1990 | Sagel |
| 5,088,706 A | * | 2/1992 | Jackson ............ 5/608 |
| 5,131,105 A | | 7/1992 | Harrawood et al. |
| 5,131,106 A | * | 7/1992 | Jackson ............ 5/613 |
| 5,161,267 A | | 11/1992 | Smith |
| 5,163,890 A | | 11/1992 | Perry, Jr. |
| 5,181,289 A | | 1/1993 | Kassai |
| 5,208,928 A | | 5/1993 | Kuck et al. |
| 5,210,887 A | | 5/1993 | Kershaw |
| 5,210,888 A | | 5/1993 | Canfield |
| 5,230,112 A | | 7/1993 | Harrawood et al. |
| 5,231,741 A | | 8/1993 | Maguire |
| 5,239,716 A | | 8/1993 | Fisk |
| 5,274,862 A | | 1/1994 | Palmer, Jr. |
| 5,333,334 A | | 8/1994 | Kassai |
| 5,393,018 A | | 2/1995 | Roth et al. |
| 5,444,882 A | | 8/1995 | Andrews et al. |
| 5,461,740 A | | 10/1995 | Pearson |
| 5,468,216 A | | 11/1995 | Johnson et al. |
| 5,487,195 A | | 1/1996 | Ray |
| 5,499,408 A | | 3/1996 | Nix |
| 5,524,304 A | | 6/1996 | Shutes |
| 5,544,371 A | | 8/1996 | Fuller |
| 5,579,550 A | | 12/1996 | Bathrick et al. |
| 5,588,705 A | | 12/1996 | Chang |
| 5,613,254 A | | 3/1997 | Clayman et al. |
| 5,640,730 A | | 6/1997 | Godette |
| 5,645,079 A | | 7/1997 | Zahiri et al. |
| 5,658,315 A | | 8/1997 | Lamb et al. |
| 5,659,909 A | | 8/1997 | Pfeuffer et al. |
| 5,673,443 A | | 10/1997 | Marmor |
| 5,737,781 A | | 4/1998 | Votel |
| 5,754,997 A | | 5/1998 | Lussi et al. |
| 5,774,914 A | | 7/1998 | Johnson et al. |
| 5,794,286 A | | 8/1998 | Scott et al. |
| 5,862,549 A | | 1/1999 | Morton et al. |
| 5,870,784 A | | 2/1999 | Elliott |
| 5,890,238 A | | 4/1999 | Votel |
| 5,901,388 A | | 5/1999 | Cowan |
| 5,937,456 A | | 8/1999 | Norris |
| 5,996,151 A | | 12/1999 | Bartow et al. |
| 6,000,076 A | | 12/1999 | Webster et al. |
| 6,035,465 A | | 3/2000 | Rogozinski |
| 6,049,923 A | | 4/2000 | Ochiai |
| 6,212,713 B1 | | 4/2001 | Kuck et al. |
| 6,260,220 B1 | | 7/2001 | Lamb et al. |
| 6,282,736 B1 | | 9/2001 | Hand et al. |
| 6,282,738 B1 | | 9/2001 | Heimbrock et al. |
| 6,286,164 B1 | | 9/2001 | Lamb et al. |
| 6,295,671 B1 | | 10/2001 | Reesby et al. |
| 6,322,251 B1 | | 11/2001 | Ballhaus et al. |
| 6,438,777 B1 | | 8/2002 | Bender |
| 6,496,991 B1 | | 12/2002 | Votel |
| 6,499,162 B1 | | 12/2002 | Lu |
| 6,505,365 B1 | | 1/2003 | Hanson et al. |
| 6,526,610 B1 | | 3/2003 | Hand et al. |
| 6,634,043 B2 | | 10/2003 | Lamb et al. |
| 6,638,299 B2 | | 10/2003 | Cox |
| 6,662,388 B2 | | 12/2003 | Friel |
| 6,668,396 B2 | | 12/2003 | Wei |
| 6,681,423 B2 | | 1/2004 | Zachrisson |
| 6,701,553 B1 | | 3/2004 | Hand et al. |
| 6,791,997 B2 | | 9/2004 | Beyer et al. |
| 6,854,137 B2 | | 2/2005 | Johnson |
| 6,857,144 B1 | | 2/2005 | Huang |
| 6,862,759 B2 | | 3/2005 | Hand et al. |
| 6,885,165 B2 | | 4/2005 | Henley et al. |
| 6,971,131 B2 | | 12/2005 | Bannister |
| 7,003,828 B2 | | 2/2006 | Roussy |
| 7,055,195 B2 | | 6/2006 | Roussy |
| 7,089,612 B2 | | 8/2006 | Rocher et al. |
| 7,103,931 B2 | | 9/2006 | Somasundaram et al. |
| 7,137,160 B2 | | 11/2006 | Hand et al. |
| 7,171,709 B2 | | 2/2007 | Weismiller |
| 7,189,214 B1 | | 3/2007 | Saunders |
| 7,197,778 B2 | | 4/2007 | Sharps |
| 7,331,557 B2 | | 2/2008 | Dewert |
| 7,343,635 B2 | | 3/2008 | Jackson |
| 7,428,760 B2 | | 9/2008 | McCrimmon |
| 7,552,490 B2 | | 6/2009 | Saracen et al. |
| 7,596,820 B2 | | 10/2009 | Nielsen et al. |
| 7,653,953 B2 | * | 2/2010 | Lopez-Sansalvador ......... 5/607 |
| 7,669,262 B2 | | 3/2010 | Skripps et al. |
| 7,874,695 B2 | | 1/2011 | Jensen |
| 8,060,960 B2 | | 11/2011 | Jackson |
| 8,677,529 B2 | | 3/2014 | Jackson |
| 8,719,979 B2 | | 5/2014 | Jackson |

(56) References Cited

U.S. PATENT DOCUMENTS

| | | | |
|---|---|---|---|
| 8,826,474 | B2 | 9/2014 | Jackson |
| 8,826,475 | B2 | 9/2014 | Jackson |
| 8,839,471 | B2 | 9/2014 | Jackson |
| 8,844,077 | B2 * | 9/2014 | Jackson et al. ............... 5/607 |
| 8,856,986 | B2 | 10/2014 | Jackson |
| 8,938,826 | B2 | 1/2015 | Jackson |
| 8,978,180 | B2 | 3/2015 | Jackson |
| 2001/0037524 | A1 | 11/2001 | Truwit |
| 2002/0023298 | A1 | 2/2002 | Lamb et al. |
| 2003/0055456 | A1 | 3/2003 | Cox |
| 2003/0074735 | A1 | 4/2003 | Zachrisson |
| 2004/0098804 | A1 | 5/2004 | Varadharajulu et al. |
| 2004/0133983 | A1 | 7/2004 | Newkirk et al. |
| 2006/0016010 | A1 | 1/2006 | Weismiller |
| 2006/0080777 | A1 | 4/2006 | Rocher et al. |
| 2006/0123546 | A1 | 6/2006 | Horton et al. |
| 2006/0185090 | A1 | 8/2006 | Jackson |
| 2007/0107126 | A1 | 5/2007 | Koch et al. |
| 2007/0113336 | A1 * | 5/2007 | Sharps ................. 5/81.1 R |
| 2007/0192960 | A1 | 8/2007 | Jackson |
| 2008/0000028 | A1 | 1/2008 | Lemire et al. |
| 2008/0216241 | A1 | 9/2008 | Mangiardi |
| 2009/0126116 | A1 | 5/2009 | Lamb et al. |
| 2010/0192300 | A1 | 8/2010 | Tannoury et al. |
| 2010/0293713 | A1 * | 11/2010 | Sharps et al. ............... 5/86.1 |
| 2011/0099716 | A1 | 5/2011 | Jackson |
| 2011/0107516 | A1 | 5/2011 | Jackson |
| 2011/0107517 | A1 | 5/2011 | Lamb et al. |
| 2012/0198625 | A1 | 8/2012 | Jackson |
| 2012/0246829 | A1 | 10/2012 | Lamb et al. |
| 2012/0255122 | A1 | 10/2012 | Diel et al. |
| 2013/0111666 | A1 | 5/2013 | Jackson |
| 2013/0133137 | A1 | 5/2013 | Jackson |
| 2013/0198958 | A1 | 8/2013 | Jackson et al. |
| 2013/0205500 | A1 | 8/2013 | Jackson |
| 2013/0219623 | A1 | 8/2013 | Jackson |
| 2013/0254995 | A1 | 10/2013 | Jackson |
| 2013/0254996 | A1 | 10/2013 | Jackson |
| 2013/0254997 | A1 | 10/2013 | Jackson |
| 2013/0312187 | A1 | 11/2013 | Jackson |
| 2013/0326813 | A1 | 12/2013 | Jackson |
| 2014/0007349 | A1 | 1/2014 | Jackson |
| 2014/0020181 | A1 | 1/2014 | Jackson |
| 2014/0173826 | A1 | 6/2014 | Jackson |
| 2014/0196212 | A1 | 7/2014 | Jackson |
| 2014/0201913 | A1 | 7/2014 | Jackson |
| 2014/0201914 | A1 | 7/2014 | Jackson |
| 2014/0208512 | A1 | 7/2014 | Jackson |
| 2014/0317847 | A1 | 10/2014 | Jackson |
| 2015/0059094 | A1 | 3/2015 | Jackson |

FOREIGN PATENT DOCUMENTS

| | | |
|---|---|---|
| GB | 810956 | 3/1959 |
| JP | S53763 | 1/1978 |
| JP | 2000060995 | 2/2000 |
| WO | 9907320 | 2/1999 |
| WO | 0062731 | 10/2000 |
| WO | WO 00/62731 | 10/2000 |
| WO | 0160308 | 8/2001 |
| WO | 03070145 | 8/2003 |
| WO | WO 2007/130679 A2 | 11/2007 |
| WO | 2009054969 | 4/2009 |
| WO | 2009100692 | 8/2009 |

OTHER PUBLICATIONS

Brochure of Smith & Nephew on Spinal Positioning System, 2003, 2004.
Pages from website http://www.schaerermayfieldusa.com, pp. 1-5, date of first publication: Unknown.
Complaint for Patent Infringement, *Jackson v. Mizuho Orthopedic Sys., Inc.*, No. 4:12-CV-01031 (W.D, Mo. Aug. 7, 2012).
First Amended Complaint for Patent Infringement and Correction of Inventorship, *Jackson v. Mizuho Orthopedic Sys., Inc.*, No. 4:12-CV-01031 (W.D. Mo. Sep. 21, 2012).
Defendant Mizuho Orthopedic Systems, Inc.'s Answer to First Amended Complaint and Counterclaims, *Jackson v. Mizuho Orthopedic Sys., Inc.*, No. 4:12-CV-01031 (W.D. Mo. Nov. 1, 2012).
Plaintiff Roger P. Jackson, MD's, Reply to Counterclaims, *Jackson v. Alizuho Orthopedic Sys., Inc.*, No. 4:12-CV-01031 (W.D. Mo. Nov. 26, 2012).
Roger P. Jackson's Disclosure of Asserted Claims and Preliminary Infringement Contentions, *Jackson v. Mizuho Orthopedic Sys., Inc.*, No. 4:12-CV-01031 (W.D. Mo. Jan. 4, 2013).
Second Amended Complaint for Patent Infringement, for Correction of Inventorship, For Breach of a Non-Disclosure and Confidentiality Agreement, and for Misappropriation of Dr. Jackson's Right of Publicity, *Jackson v. Mizuho Orthopedic Sys, Inc.*, No. 4:12-CV-01031 (W.D. Mo. Jan. 28, 2013).
Defendant Mizuho Orthopedic Systems, Inc.'s Answer to Second Amended Complaint and Counterclaims, *Jackson v. Mizuho Orthopedic Sys., Inc.*, No. 4:12-CV-01031 (W.D. Mo. Feb. 19, 2013).
Defendant Mizuho Osi's Invalidity Contentions Pursuant to the Parties' Joint Scheduling Order, *Jackson v. Mizuho Orthopedic Sys., Inc.*, No. 4:12-CV-01031 (W.D. Mo. Feb. 22, 2013).
Plaintiff Roger P. Jackson, MD's Reply to Second Counterclaims, *Jackson v. Mizuho Orthopedic Sys., Inc.*, No. 4:12-CV-01031 (W.D. Mo. Mar. 12, 2013).
Roger P. Jackson Md's Disclosure of Proposed Terms to Be Construed, *Jackson v. Mizuho Orthopedic Sys., Inc.*, No. 4:12-CV-01031 (W.D. Mo. Apr. 5, 2013).
Defendant Mizuho Orthopedic Systems, Inc.'s Disclosure of Proposed Terms and Claim Elements for Construction, *Jackson v. Mizuho Orthopedic Sys., Inc.*, No. 4:12-CV-01031 (W.D. Mo. Apr. 5, 2013).
Mizuho Orthopedic Systems, Inc.'s Disclosure of Proposed Claim Constructions and Extrinsic Evidence, *Jackson v. Mizuho Orthopedic Sys., Inc.*, No. 4:12-CV-01031 (W.D. Mo. May 13, 2013).
Plaintiff Roger P. Jackson, MD's Disclosure of Preliminary Proposed Claim Constructions, *Jackson v. Mizuho Orthopedic Sys., Inc.*, No. 4:12-CV-01031 (W.D. Mo. May 13, 2013).
Defendant Mizuho Osi's Amended Invalidity Contentions Pursuant to the Parties' Joint Scheduling Order, *Jackson v. Mizuho Orthopedic Sys., Inc.*, No. 4:12-CV-01031 (W.D. Mo. May 15, 2013).
Joint Claim Construction Chart and Joint Prehearing Statement, *Jackson v. Mizuho Orthopedic Sys., Inc.*, No. 4:12-CV-01031 (W.D. Mo. Jun. 7, 2013).
Defendant Mizuho Orthopedic Systems, Inc.'s Objections and Responses to Plaintiff's First Set of Interrogatories, *Jackson v. Mizuho Orthopedic Sys., Inc.*, No. 4:12-CV-01031 (W.D. Mo. Jun. 24, 2013).
Defendant Mizuho Orthopedic Systems, Inc.'s Opening Claim Construction Brief, *Jackson v. Mizuho Orthopedic Sys., Inc.*, No. 4.12-CV-01031 (W.D. Mo. Jul. 31, 2013).
Plaintiff Roger P. Jackson, MD's Opening Claim Construction Brief, *Jackson v. Mizuho Orthopedic Sys., Inc.*, No. 4:12-CV-01031 (W.D. Mo. Jul. 31, 2013).
Appendix A Amended Infringement Contentions Claim Chart for Mizuho's Axis System Compared to U.S. Pat. No. 7,565,708, *Jackson v. Mizuho Orthopedic Sys., Inc.*, No. 4:12-CV-01031 (W.D. Mo, Aug. 12, 2013).
Appendix B Amended Infringement Contentions Claim Chart for Mizuho's Axis System Compared to U.S. Pat. No. 8,060.960, *Jackson v. Mizuho Orthopedic Sys., Inc.*, No. 4:12-CV-01031 (W.D. Mo. Aug. 12, 2013).
Appendix C Amended Infringement Contentions Claim Chart for Mizuho's Proaxis System Compared to U.S. Pat. No. 7,565,708, *Jackson v. Mizuho Orthopedic Sys., Inc.*, No. 4:12-CV-01031 (W.D. Mo. Aug. 12, 2013).
Appendix D Amended Infringement Contentions Claim Chart for Mizuho's Proaxis System Compared to U.S. Pat. No. 8,060,960, *Jackson v. Mizuho Orthopedic Sys., Inc.*, No. 4:12-CV-01031 (W.D. Mo. Aug. 12, 2013).

(56) References Cited

OTHER PUBLICATIONS

Plaintiff Roger P. Jackson, MD's Responsive Claim Construction Brief, *Jackson v. Mizuho Orthopedic Sys., Inc.*, No. 4:12-CV-01031 (W.D, Mo. Aug. 16, 2013).
Defendant Mizuho Orthopedic Systems, Inc's Brief in Response to Plaintiff's Opening Claim Construction Brief, *Jackson v. Mizuho Orthopedic Sys., Inc.*, No. 4:12-CV-01031 (W.D. Mo. Aug. 16, 2013).
Plaintiff Roger P. Jackson, Md's Suggestions in Support of His Motion to Strike Exhibit A of Mizuho's Opening Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc.'s Opposition to Plaintiffs Motion to Strike, *Jackson v. Mizuho Orthopedic Sys., Inc.*, No. 4:12-CV-01031 (W.D. Mo. Sep. 3, 2013).
Transcript of Claim Construction Hearing, *Jackson v. Mizuho Orthopedic Sys., Inc.*, 4:12-CV-01031 (W.D. Mo. Oct. 11, 2013).
Plaintiff Roger P. Jackson, MD's Claim Construction Presentation for U.S. District Judge Nanette K. Laughrey, *Jackson v. Mizuho Orthopedic Sys., Inc.*, No. 4:12-CV-01031 (W.D. Mo. Oct. 11, 2013).
Mizuho's Claim Construction Argument, *Jackson v. Mizuho Orthopedic Sys., Inc.*, No. 4:12-CV-01031 (W.D. Mo. Oct. 11, 2013).
Order, *Jackson v. Mizuho Orthopedic Sys., Inc.*, No. 4:12-CV-01031 (W.D. Mo. Apr. 4, 2014).
European Search Report, EP11798501.0, dated Mar. 30, 2015.
Japanese Office Action, JP 2014-132463, dated Jun. 18, 2015.
Japanese Office Action, JP 2014-142074, dated Jun. 18, 2015.
European Examination Report, EP11798501.0, dated Nov. 12, 2015.
Japanese Final Rejection (English version), JP 2014-142074, dated Dec. 6, 2015.
International Search Report and Written Opinion of the International Searching Authority, PCT/US2015/039400, dated Dec. 7, 2015, 13 pages.

\* cited by examiner

SYNCHRONIZED PATIENT ELEVATION AND POSITIONING APPARATUS FOR USE WITH PATIENT POSITIONING SUPPORT SYSTEMS

CROSS-REFERENCE TO RELATED APPLICATIONS

This application claims the benefit of U.S. Provisional Application No. 61/742,167 filed Aug. 3, 2012 and entitled "Synchronized Patient Elevation And Positioning Apparatus For Use With Patient Positioning Support Systems," the entirety of which is incorporated by reference herein.

This application is also a Continuation-In-Part of U.S. patent application Ser. No. 13/317,012, now U.S. Pat. No. 8,719,979, which is a Continuation of U.S. patent application Ser. No. 12/460,702, now U.S. Pat. No. 8,060,960, and also which is a Continuation of U.S. patent application Ser. No. 11/788,513, now U.S. Pat. No. 7,565,708, each of which is incorporated by reference herein in its entirety.

U.S. patent application Ser. No. 11/788,513 claims the benefit of U.S. Provisional Application No. 60/798,288, and is also a Continuation-In-Part of U.S. patent application Ser. No. 11/159,494, now U.S. Pat. No. 7,343,635, which is a Continuation-In-Part of U.S. patent application Ser. No. 11/062,775, now U.S. Pat. No. 7,152,261 the entirety of which are incorporated by reference herein.

BACKGROUND OF THE INVENTION

The present invention is directed to a patient positioning apparatus for positioning a patient on a patient support structure, such as a surgical table, for a medical procedure. In particular, the present invention is directed to an apparatus for performing a "sandwich and roll" procedure while transferring a patient in a supine position from a bed, gurney or trolley to a prone position on the surgical table.

Certain surgical procedures require changing a patient's body position during said procedure. For example, spinal surgery may require turning the patient over from a prone position to a supine position, and vice versa. When a standard surgical table is used, turning the patient over, or taking a radiograph, often requires transferring the patient between the surgical table and another support, and then back again. Such transfer procedures interrupt the surgical procedure, are cumbersome, and may compromise the surgical site.

Some modern surgical tables, such as modular, multi-articulated patient support systems, have been developed for supporting the patient in a variety of positions and for moving the patient's body in various ways during a surgical procedure, including articulating the patient at the hips, placing the patient in Trendelenburg and reverse-Trendelenburg positions, tilting the patient, and turning the patient over. Such patient support systems typically include a base with a pair of independently adjustable telescoping columns that are connected by and support an articulatable patient support or table top. The patient support may be raised and lowered, tilted and rotated about a longitudinal axis in horizontal and tilted orientations. During some surgeries, a traditional closed patient support is replaced with an open frame patient support that allows the patient's abdomen to depend therethrough.

U.S. Pat. No. 7,152,261 to Jackson, incorporated herein by reference in its entirety, describes a closed frame modular, multi-articulated patient support system with independently adjustable head- and foot-end telescoping risers, which are connected by an adjustable cross-beam, and which support a patient support structure that may be raised, lowered and rotated about a longitudinal axis in various horizontal and tilted orientations. A secondary elevator enables lowering of the foot-end of the patient support to near the floor. A patient placed on the patient support can be rotated 180° after installation of a stationary riser and an imaging table that sandwiches the patient against the patient support.

U.S. Pat. No. 7,565,708 to Jackson, incorporated herein by reference in its entirety, describes an infinitely adjustable open-frame patient support system, wherein the frame can be articulated near a middle thereof, as well as being raised, lowered and rotated about a longitudinal axis in various horizontal and tilted orientations. An imaging table may be attached to and spaced from the patient support, for turning the patient 180°, however, the distance between the patient support and the imaging table must be adjusted manually.

Prior to a surgical procedure, a patient is usually anaesthetized and then place of the patient support. Since the patient starts in a supine position on a gurney, also referred to as a trolley or a stretcher, and must be transferred to a prone position on an open frame support, such positioning procedures can be quite difficult. Accordingly, there is a need for an apparatus for positioning a patient on a surgical table in the prone position.

SUMMARY OF THE INVENTION

In a first embodiment of the present invention, a patient positioning apparatus is provided for performing a "sandwich and roll" procedure while positioning a patient in a prone position on a patient support structure. Generally, a patient support structure is as a surgical table having a base with spaced head-end and foot-end elevator subassemblies that removably supports an attached patient support frame that can be rotated about a longitudinal roll axis a distance of up to at least about ±180°. The patient support frame includes either a traditional closed table top or an open frame that allows the patient's abdomen to depend therethrough. The patient positioning apparatus includes head-end and foot-end lift subassemblies that are removably attached to the ends of a transfer table. The head-end and foot-end lift subassemblies are attached to the surgical table head-end and foot-end elevator subassemblies, respectively, such that the transfer table is spaced from the patient support frame. Each lift apparatus includes a gear mechanism, with a lead nut that engages a lead screw, for moving the transfer table toward and away from the patient support frame. An actuator synchronizes the lift subassemblies, so as to maintain the transfer table in a substantially level orientation, relative to the longitudinal roll axis or the floor.

In a further embodiment of the patient positioning apparatus, the transfer table includes a frame joined with a tabletop member. The frame includes a pair of spaced support beams joined by head-end and foot-end cross-beams, and cross-beam brackets for releasable hinged attachment to the head-end and foot-end lift subassemblies, respectively. Quick-release pins hingedly join the brackets of the transfer table with the respective lift subassemblies.

In another further embodiment of the patient positioning apparatus, additional quick release pins removably attach the head-end and foot-end lift subassemblies to the respective head-end and foot-end elevator subassemblies.

In yet another further embodiment of the patient positioning apparatus, each of the lift subassemblies includes a pair of spaced support members; a lead screw spaced from and substantially parallel with the support members; first and second brace members, the first brace member joining a first end of each of the support members and the lead screw and the second brace member joining the second ends of each of the support members and the lead screw, the first brace member including an attachment structure for removable attachment to a respective elevator subassembly; and a carrier member slidably engaging the support members. The carrier member includes a gear subassembly and a bracket. The gear subassembly operably engages the lead screw so as to move the carrier member in a direction selected from toward and away from the first brace member, or toward and away from the longitudinal roll axis. The bracket releasably hingeably attaches the carrier member and the associated lift subassembly to the transfer table.

In a still further embodiment of the patient positioning apparatus, the lead screw is an ACME screw.

In another further embodiment of the patient positioning apparatus, the gear subassembly includes a lead nut that rotatably engages the lead screw, and a motor connector for operable engagement of an external motor.

In still another further embodiment of the patient positioning apparatus, the carrier member includes a pair of sliding brackets, each of which is sized and shaped to slidably engage a support member. In a further embodiment, a bushing is located between each sliding bracket and a respective support member.

In a second embodiment of the invention, a method of transferring a patient to a medical patient support structure in a prone position is provided, wherein the patient support structure includes a base with spaced head-end and foot-end elevator subassemblies, a patient support frame removably attached to and supported by the elevator subassemblies, and a rotation mechanism for rotating the patient support frame about a longitudinally extending roll axis a distance of up to at least 180°. The method includes the steps of providing a patient positioning apparatus having head-end and foot-end lift subassemblies and a transfer table; releasably attaching the patient positioning apparatus to the patient support structure; orienting the patient positioning apparatus for patient transfer; placing a patient on the transfer table in a supine position; actuating the head-end and foot-end lift subassemblies so as to move the patient toward the patient support frame, such that the patient is snugly sandwiched between the transfer table and the patient support frame; rotating the patient support structure to the first position, such that the patient supported by the patient support frame in a prone position; and detaching the patient positioning apparatus from the patient support structure.

In a further embodiment of the second embodiment, the step of releasably attaching the patient positioning apparatus to the patient support structure includes attaching the head-end lift subassembly to the head-end elevator subassembly; attaching the foot-end lift subassembly to both the foot-end elevator subassembly; and attaching the transfer table to the head end and foot-end lift subassemblies.

In another further embodiment of the second embodiment, the step of orienting the patient positioning apparatus for patient transfer includes rotating the patient support structure from a first position about 180° about the roll axis such that the transfer table is located below the patient support frame.

In another further embodiment of the second embodiment, the step of actuating the head-end and foot-end lift subassemblies includes actuating a gear subassembly so as to rotate a lead nut relative to a lead screw.

In a third embodiment of the invention, a lifting subassembly for a patient positioning apparatus having a base and a patient support structure, is provided and includes a lifting subassembly that is reversibly attachable to the base and has first and second lifting positions with respect to the base. The lifting subassembly is adapted to move the patient support structure from the first lifting position to the second lifting position in a vertical direction above a floor, and the lifting subassembly is also reversibly rotatably from a first vertical position to a second vertical position with respect to the base.

In a further embodiment of the third embodiment, the lifting subassembly is removable when in the second vertical position.

In another further embodiment of the third embodiment, the lifting subassembly includes a pair of spaced parallel elongate support members, wherein each support member has first and second ends; and spaced parallel first and second brace members. The first brace member joins the first ends of the support members and the second brace member joins the second ends of the support members, so as to provide a frame structure. The lifting subassembly also includes a carrier member that is located between the brace members and is reversibly movable along a length of the support members, whereby the patient support structure is slidingly moved between the first and second lifting positions.

In another further embodiment of the third embodiment, the lifting subassembly includes a lifting mechanism that is adapted to move the carrier member.

In still another further embodiment, the lifting mechanisms includes a lead screw that is spaced from and parallel with the support members and joined with the brace members, and a gear subassembly that engages the lead screw so as to move the carrier member along the length of the support members. In some further embodiments, the carrier member includes at least one engagement member that is adapted for reversibly engaging the patient support structure. In some further embodiments, the carrier member includes a pair of spaced parallel ring members. Each of the ring members includes a through-bore that slidingly receives one of the elongate support members therethrough, such that the carrier member is movable between the brace members. In some further embodiments, at least one of the brace members includes a connection portion adapted for reversible engagement of the base structure.

In another further embodiment of the third embodiment, the lifting subassembly includes a pair of lifting subassemblies. The lifting subassembly includes an actuator, in some embodiments.

In a fourth embodiment, a patient positioning apparatus is provided for positioning a patient on a patient support structure for a medical procedure. The patient support structure has a base that supports a removably attachable patient support frame above a floor and a rotation mechanism for rotating the patient support frame about a longitudinally extending roll axis and between first and second vertical positions with respect to the floor. The patient positioning apparatus includes a lifting subassembly that is reversibly attachable to the base and has a connection portion that is slidingly movable between the first and second lifting positions with respect to a length of the lifting subassembly. The patient positioning apparatus also includes a transfer table that is sized and shaped for receiving and supporting a patient thereon and that is reversibly attachable to the lifting subassembly.

In a further embodiment of the fourth embodiment, the apparatus includes an actuator for actuating the lifting subassembly, so as to move the transfer table between the first and second lifting positions. In a further embodiment, the transfer table includes a bracket for reversible attachment to the lifting subassembly. In some embodiments, the transfer table includes radio-transparent tabletop member.

In a further embodiment of the fourth embodiment, the lifting subassembly includes first and second lifting subassemblies. In a still further embodiment, the first and second lifting subassemblies are independently movable.

In a further embodiment of the fourth embodiment, each of the lift subassemblies includes a pair of spaced apart and substantially parallel support members; a lead screw that is spaced from and substantially parallel with the support members; a first brace member that joins a first end of each of the support members and the lead screw, the first brace member includes an attachment structure for removable attachment to a respective vertical support subassembly. The second brace member joins a second end of each of the support members and the jack screw; and a carrier member that slidably engages the support members. The carrier member has a gear subassembly that operably engages the lead screw so as to reversibly move the carrier member toward and away from the first brace member, and a bracket for releasable hingeable attachment to the transfer table.

In a further embodiment of the fourth embodiment, the gear subassembly includes a lead nut rotatably engaging the lead screw; and a motor connector for operable engagement of an external motor.

In a further embodiment of the fourth embodiment, the carrier member includes a pair of sliding brackets. Each of the sliding bracket is sized and shaped to slidably engage a support member.

In a further embodiment of the fourth embodiment, the apparatus also includes an actuator that is adapted to synchronously actuate the first and second lifting subassemblies, so as to maintain the transfer table in a plane substantially parallel to the roll axis while moving the transfer table between the first and second lifting positions.

In a still further embodiment, one of the first and second lifting positions is closer to the patient support structure than the other of the first and second lifting positions.

In a still further embodiment, when in the closer of the first and second lifting positions, a patient on the transfer table is substantially sandwiched between the transfer table and the patient support structure.

Various objects and advantages of this invention will become apparent from the following description taken in relation to the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawings, a patient positioning apparatus of the present invention is generally denoted by the numeral 1. The patient positioning apparatus is useful for positioning a patient 2 in a prone position on a patient support structure 4, or surgical table, such as for a medical procedure. An exemplary patient support structure 4 is shown in FIGS. 8-13.

Numerous patient support structures 4 find use with the patient positioning apparatus 1 of the present invention, including those described in U.S. Pat. Nos. 7,152,261, 7,343,635, 7,565,708, and 7,739,762, and also U.S. Publication No. 2009-0282614, U.S. patent application Ser. No. 12/803,525, filed on Jun. 22, 2010 and entitled "Surgery Table Apparatus," U.S. patent application Ser. No. 12/803,173, filed on Jun. 21, 2010 and entitled "Patient Positioning Support Structure," U.S. patent application Ser. No. 12/803,192, filed on Sep. 9, 2010 and entitled "Patient Positioning Support Structure," and U.S. patent application Ser. No. 13/317,012, filed on Oct. 6, 2011 and entitled "Patient Positioning Support Structure," all of which are incorporated by reference herein in their entirety.

Figure 8:
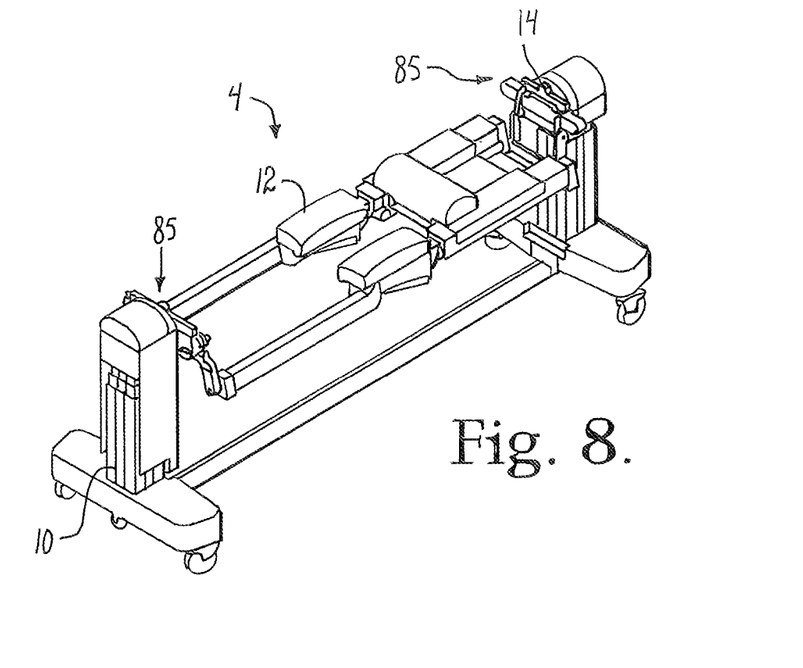
FIG. 8 is a perspective view of an exemplary patient support structure, or surgical table, for use with the patient positioning apparatus of FIG. 1.

The exemplary patient support structure 4 depicted in FIG. 8 is a fully adjustable, multi-articulatable and rotatable surgical table that is used during a variety of surgical procedures that require one or more of: moving the patient between supine and prone positions, bending the patient at the hips, placing the patient in a Trendelenburg or reverse-Trendelenburg position, and moving the patient among various tilted and rotated positions. Such surgical procedures include but are not limited to orthopedic and spinal surgical procedures. The illustrated patient support structure 4 includes a base 6 with spaced head-end and foot-end elevator subassemblies 8 and 10, respectively, removably attached to and supporting a patient support frame 12. As is known in the art, in some circumstances, the open patient support frame 12 may be replaced with a traditional closed table top or an imaging table top.

At least one of the illustrated patient support structure elevator subassemblies 8, 10 includes a rotation mechanism 14 for rotating the patient support frame 12 about a longitudinally extending roll axis R, which extends between rotational pivot points P of the patient support structure 4. The rotational mechanism 14 advantageously enables infinitely adjustable rotation and tilting of the patient support frame 12 a distance or amount of up to at least ±180° from a first position. Such tilting provides improved access to the patient 2, and enables turning the patient 2 over between prone and supine positions, for surgical access to the patient's front and back without removing the patient 2 from the frame 12. Some patient support structures 4 are configured such that the patient support frame 12 is rotatable up to at least 360° in either direction.

Referring now to FIGS. 1-7, the patient positioning apparatus 4 includes a transfer table 20, a pair of spaced lift subassemblies, such as head-end and foot-end lift subassemblies 24 and 26, and an actuator 26, all of which are described in greater detail below.

Figure 9:
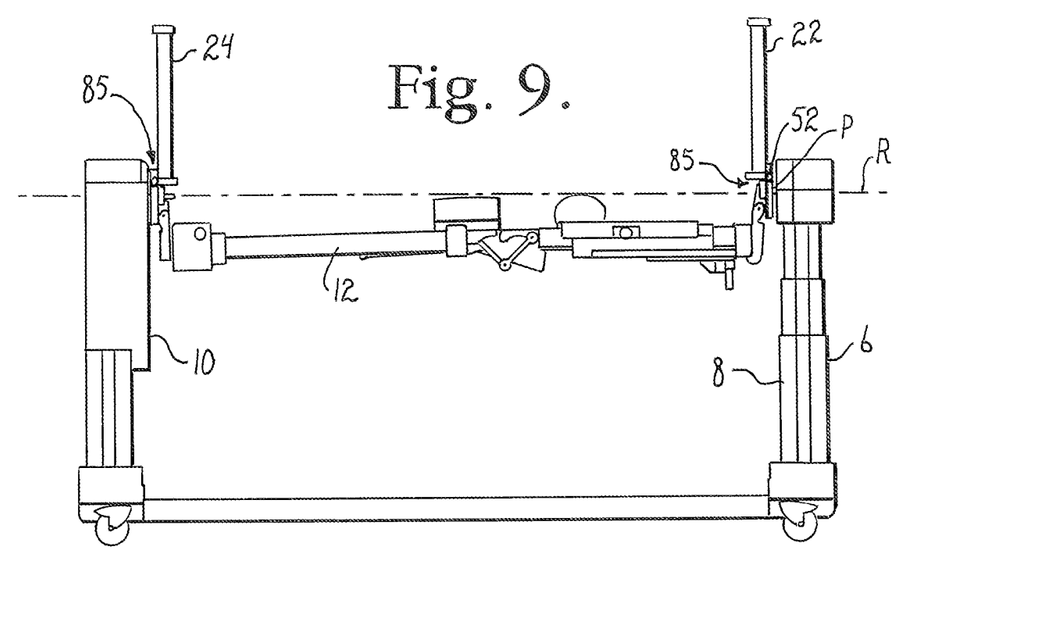
FIG. 9 is a side view of the patient support structure of FIG. 8, with head-end and foot-end lift subassemblies of the patient positioning apparatus attached thereto.

The head-end and foot-end lift subassemblies 22 and 24 are removably attachable to the head-end and foot-end elevator subassemblies 8 and 10, respectively, such as shown in FIG. 9. The head-end and foot-end lift subassemblies 22, 24 are also removably attachable to the transfer table head and foot ends 30 and 32, respectively. Each of the lift subassemblies 22 and 24 is adapted for moving the transfer table 20 in a direction selected from toward and away from the roll axis R. When being moved by the lift subassemblies 22 and 24, the transfer table 20 is maintained in a plane substantially parallel to the roll axis, since the actuator 26 is adapted to synchronously actuate the lift subassemblies 22 and 24, which is discussed in greater detail below. It is foreseen that in some circumstances, the actuator 26 may actuate the lift subassemblies 22, 24 in a non-synchronous manner, such as but not limited to singularly, independently, at different rates, and in different directions.

Figure 1:
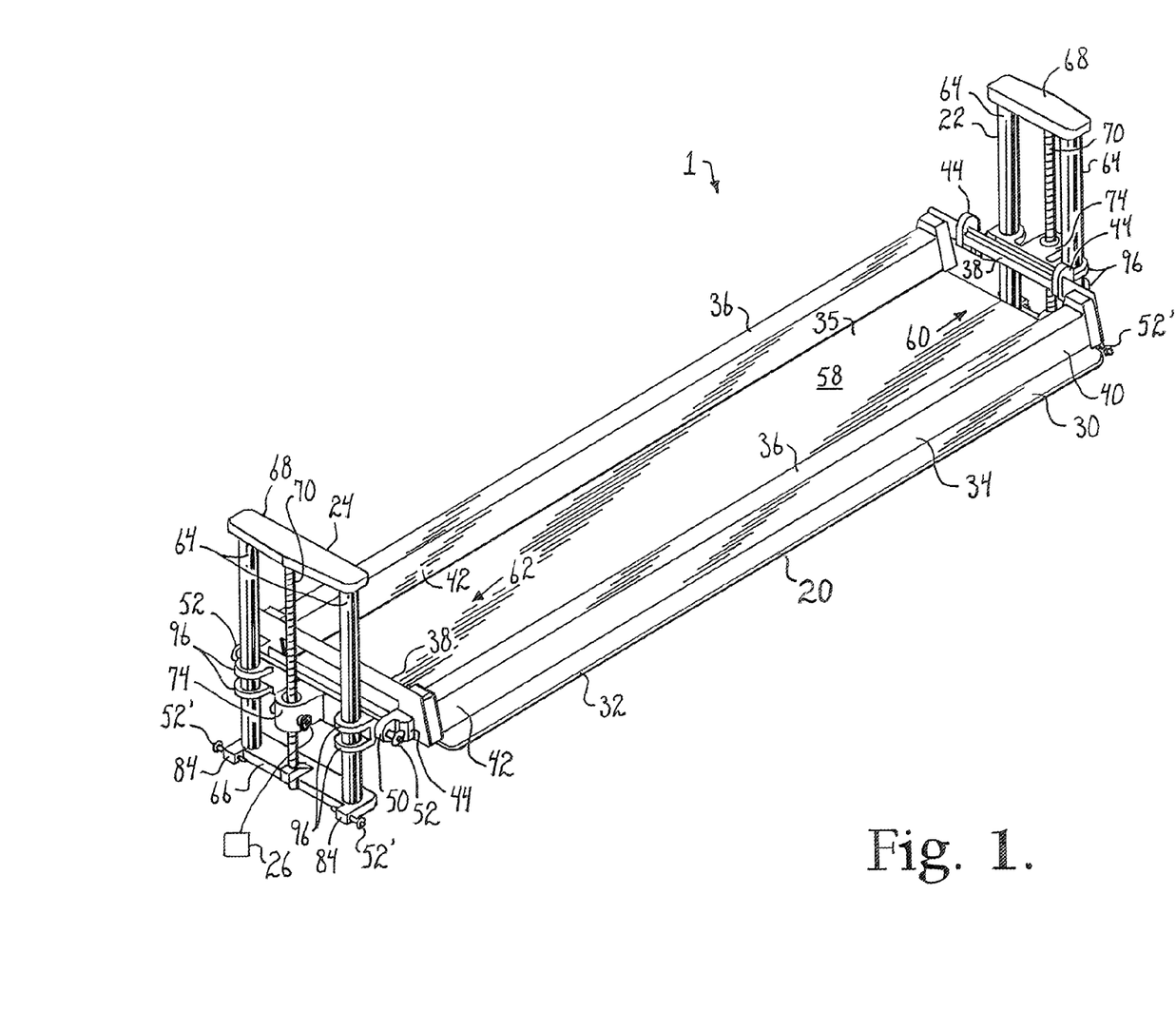
FIG. 1 is a perspective view of a patient positioning apparatus in accordance with the invention.
Figure 2:
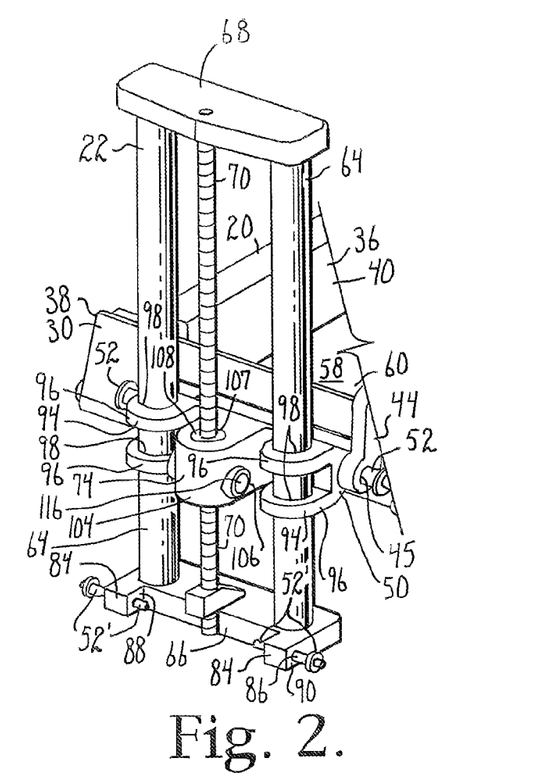
FIG. 2 is an enlarged perspective view of the outboard side of the head end of the patient positioning apparatus of FIG. 1, with portions broken away.
Figure 3:
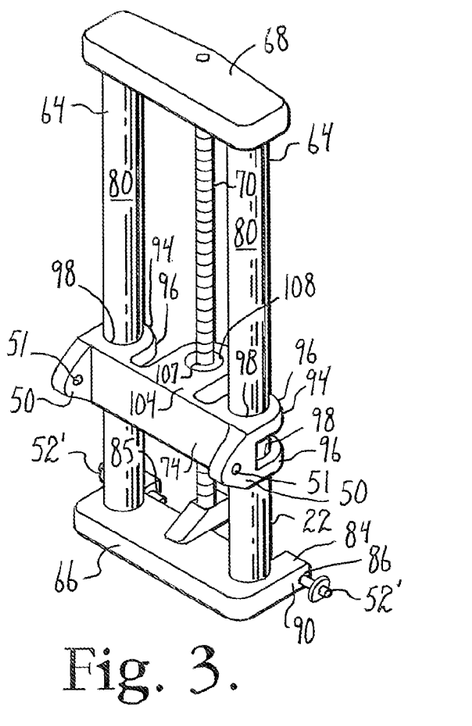
FIG. 3 is a perspective view of the inboard side of the head end of the patient positioning apparatus of FIG. 2.
Figure 5:
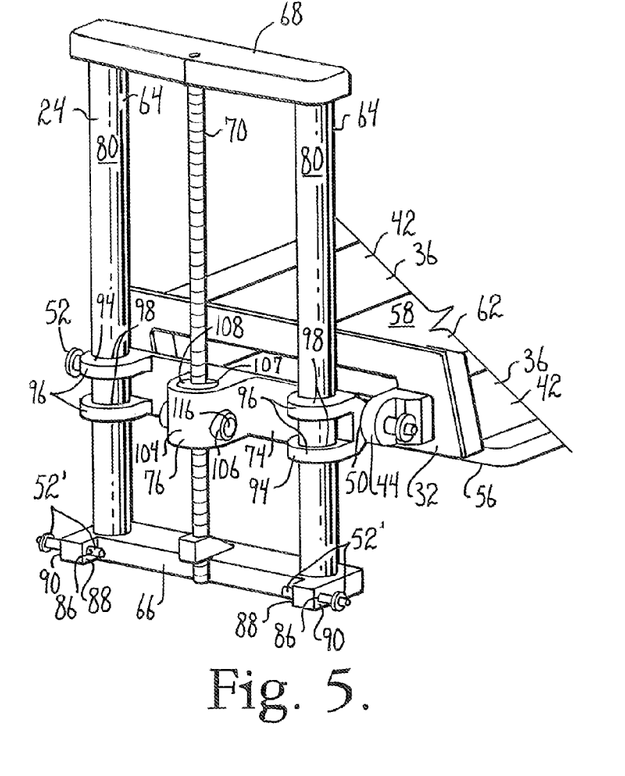
FIG. 5 is an enlarged perspective view of the outboard side of the foot end of the patient positioning apparatus of FIG. 1, with portions broken away.
Figure 6:
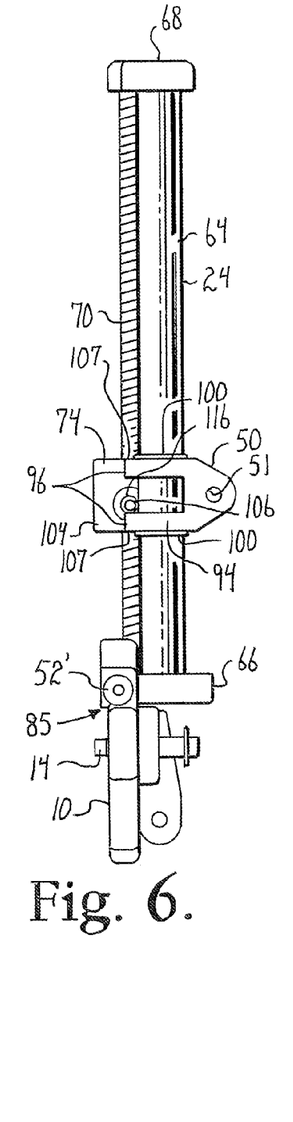
FIG. 6 is an enlarged side view of the foot end of the patient positioning apparatus of FIG. 5, wherein the patient positioning apparatus is attached to a portion of a head end of a patient positioning structure.

Referring now to FIGS. 1, 2 and 5, the transfer table 20 includes a frame 34 supporting a tabletop member 35. The frame 34 includes a pair of spaced, longitudinally extending support beams 36 joined by cross-beams 38 at their head and foot ends 40 and 42, respectively. The support beams 36 are formed of a material with a high strength-to-weight ratio, with optional radio-transparent properties, such as but not limited to carbon fiber reinforced polymers. Such materials are tough, and resilient but relatively lighter in weight. Such materials enable the surgical staff to handle the transfer table 20 without excessive strain thereto, while also enabling the transfer table 20 to withstand considerable forces caused by the weight of the patient. Each support beam 36 has a rectangular or trapezoidal cross-section, the cross-section being taken perpendicular to a longitudinal axis of the support beam 36. Such a trapezoidal shape strengthens the support beams 36 and prevents twisting due to stresses applied thereto. However, it is foreseen that the support beams 36 may have a cross-section that is circular, ovular, or any other useful shape known in the art.

The head-end and foot-end cross-beams 38 join the head and foot ends 40, 42 of the spaced support beams 36. Each cross-beam 38 includes a linkage bracket 44 with a substantially cylindrical horizontal channel 45 for releasable hinged attachment to the respective head-end and foot-end lift subassemblies 22, 24, such as described in greater detail below. Preferably, the linkage bracket 44 is a pair of spaced linkage brackets 44 that join the associated cross-beams 38 with the associated lift subassemblies 22, 24, such as is described below.

As shown in FIGS. 1, 2 and 5, the linkage brackets 44 are spaced so as to be engageable by the lift subassemblies 22, 24. Accordingly, the linkage brackets 44 are aligned with engagement brackets 50 of the associated lift subassemblies 22, 24. Each engagement bracket 50 includes a substantially cylindrical horizontal through-bore 51, which is most easily seen in FIGS. 3 and 6. The horizontal through-bores 51 are sized and shaped to receiver a quick release pin 52 therethrough. The each linkage bracket 44 is hingeably attached to a respective aligned engagement bracket 50 by axial alignment of each horizontal channel 45 with an adjacent horizontal through-bore 51, followed by insertion of a spring-loaded quick release pin 52 through the aligned horizontal channel 45 and horizontal through-bore 51. The quick release pins 52 enable the transfer table 20 to hingeably pivot with respect to the lift subassemblies 22, 24.

The tabletop member 35 has first and second sides, 56 and 58, respectively, and head- and foot-ends, which are generally denoted by the numerals 60 and 62, respectively. The tabletop member 35 is attached to the support beams 36 and optionally to the cross-beams 38, generally on its second side 58, which may also be referred to as the bottom or lower side. The patient 2 is placed upon the tabletop member first side 56, which may also be referred to as the top or upper side. The tabletop member 35 may be fabricated from any suitable resilient material known in the art, which preferably is at least one of light weight and substantially radio-transparent. In some embodiments, the tabletop member 35 is an imaging table top. It is foreseen that an imaging table may be substituted for the transfer table 20.

Referring now to FIGS. 1-7, each of the lift subassemblies includes a pair of spaced cylindrical support members 64 joined by first and second, or upper and lower, brace members 66 and 68, respectively, a lead screw 70, a gear subassembly 72 that engages the lead screw 70, and a carrier member 74 that houses the gear subassembly 72 and includes the engagement brackets 50.

The cylindrical support members 64 are cylindrically shaped solid rods or hollow tubes that extend between the first and second brace members 66 and 68, respectively. As shown in FIGS. 2, 3, 5 and 6, the support members 64 are spaced apart so as to slidingly engage the carrier member 74, which in turn is sized so as to engage either the head end 30 or the foot end 32 of the transfer table 20. The support members 64 are fabricated of a resilient and substantially rigid material that provides a substantially smooth surface 80, and preferably is also light weight, such as but not limited to carbon fiber-reinforced polymers.

The lead screw 70 is a power screw that translates turning motion of the gear subassembly 72 into the linear motion, such as upward and downward, of the transfer table 20. The lead screw 70 extends between the first and second brace members 66 and 68, and is spaced from and parallel to the support members 64. In some embodiments, the lead screw 70 is an ACME screw with a trapezoidal thread form, which offers high strength and ease of manufacture. In some embodiments, the lead screw includes a non-trapezoidal thread form. In other embodiments, the lead screw is a metric screw. As is discussed in greater detail below, the lead screw 70 engages the gear subassembly 72, which is housed within the carrier member 74. The lead screw 70 is spaced equally from each of the support members 64, so as to balance lifting power transferred through the carrier member 70 to the engagement brackets 50. Consequently, the engagement brackets 50 are moved evenly along the support members 64, with respect to the lead screw 70.

The first brace member 66 holds a first end of each of the support members 64 and of the lead screw 70 in spaced relation to one another. Additionally, the first brace member 66 joins the associated lift subassembly 22, 24 to a respective patient support structure elevator subassembly 8, 10. Each first brace member 66 includes a pair of spaced connection portions 84 for attaching the lift subassembly 22, 24 to the patient support structure 4. In the illustrated embodiment, the connection portions 84 are generally rectangularly prism-shaped and extend outwardly in an outboard direction, so as to be releasably matingly engageable by complementary attachment bracket, generally 85, of the elevator subassemblies 8, 10. However, it is foreseen that the connection portions 84 may have other three-dimensional shapes with a cross-section such as but not limited to circular, ovular, trapezoidal and rectangular.

Each connection portion 84 includes a substantially cylindrical through-bore 86 extending between its inboard and outboard sides 88, 90, respectively. The through-bores 86 are sized and shaped to receiver a quick release pin 52' therethrough. Thus, a quick release pin 52' extends from the outboard side 90 of each of the connection portion 84, through the associated through-bore 86 and outward to the inboard side 88. When attached to the patient support structure 4, each quick release pin 52' also engages an elevator subassembly attachment bracket 85 that is mated with the associated connection portion 84, so as to hold the mated bracket 85 and connection portion 84 together in a substantially rigid, non-hingeable configuration. In some embodiments, the pair of quick release pins 52' are replaced by a longer pin or rod that extends through both of the through-bores 86. Other attachment structures for attaching the lift subassemblies 22, 24 to the patient support structure flare foreseen.

The second brace member 68 holds the second ends of the support members 64 and the lead screw 70 in substantially the same spaced relation to one another as does the first brace member 66, such that the support members 64 and the lead screw 70 are oriented, configured or run substantially parallel to one another. In some embodiments, one or more of the support members 64 and the lead screw 70 extend through the second brace member 68. In other embodiments, one or more of the support members 64 and the lead screw 70 do not extend through the second brace member 68.

Referring to FIGS. 1-3 and 5, it is noted that the lift subassemblies 22 and 24 are substantially similar in their appearance, components and construction. However, the relative width of the lift subassemblies 22, 24, such as, for example the spacing between the support members 64, or the width of the brace members 66 and 68, may differ between the head and foot ends, so as to accommodate differences in spacing of the transfer table support beams 36 at their head and foot ends, or such differences between the head and foot ends of the patient support structure base 6. For example, in the illustrated embodiment, the head-end linkage brackets 44, shown in FIG. 2, are spaced closer together than are the foot-end linkage brackets 44, shown in FIG. 5. Accordingly, in this embodiment, the head-end lift subassembly support members 64 are spaced closer together than the foot-end lift subassembly support members 64. It is foreseen that in some embodiments, the spacing between the support members 64 of both of the head-end and foot-end lift subassemblies 22 and 24 are substantially the same, and that these head-end and foot-end lift subassemblies 22 and 24 may be at least one of mirror images of each other and interchangeable.

The carrier member 74 extends between and slidingly engages both of the support members 64, such that movement of the carrier member 74 is guided by the support members 64. The carrier member 74 is slidingly movable toward or away from the first brace ember 66, with respect to the support member 46. The carrier member 74 includes a pair of ring members 94, wherein a ring member 94 is associated with each of the support members 64. Each ring member 94 includes at least one ring structure 96 with a through-bore 98 through which the associated support member 64 is slidingly received. In the illustrated embodiment, each ring member 94 includes a pair of ring structures 96 that are aligned so as to be coaxial with the associated support member 64. A bushing 100 is located in each of the ring structure through-bores 96. Each of the bushings 100 includes a through-bore that receives a support member 64 therethrough, such that the bushing through-bore and the support member 64 are coaxial. The smooth inner surface of each bushing through-bore provides a bearing surface for linear motion of the associated support member 64.

Each carrier member 74 also includes a housing 104 for the gear subassembly 72, which operably engages the associated lead screw 70. As shown in FIGS. 2, 4, 5 and 7, the housing 104 shrouds the gear subassembly 72 and includes at least one access port 106 for connecting, engaging, or plugging in, the actuator 26, and axially aligned upper and lower screw openings 107 that provide a passageway for the lead screw 70 to pass through, so as to enable the gear subassembly 72 to move upward and downward along the lead screw 70. In some embodiments, a bearing 108, that is sized and shaped to fit between the screw opening 107 and the lead screw 70, constrains motion of the housing 104 relative to the lead screw 70, such as is known in the art. The bearing 108 may be any useful bearing known in the art.

Figure 4:
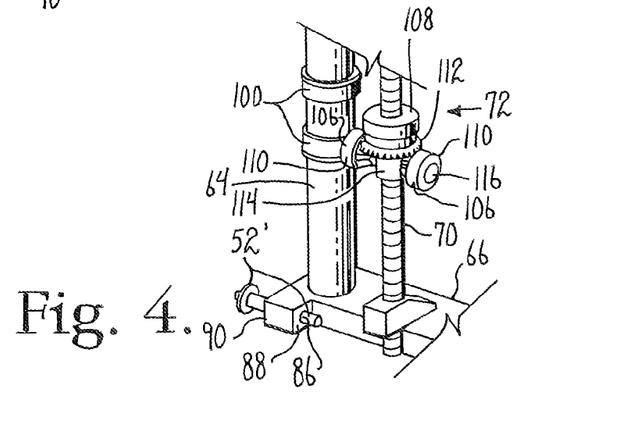
FIG. 4 is a perspective view of a portion of the apparatus of FIG. 2, with portions removed to show greater detail of the gear mechanism.
Figure 7:
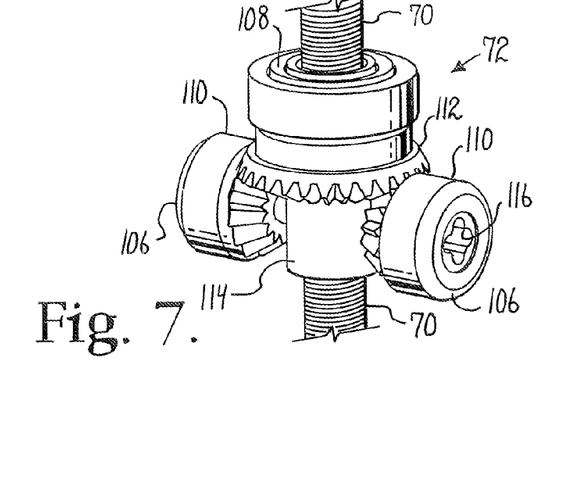
FIG. 7 is an enlarged perspective view of the gear mechanism of the patient positioning apparatus of FIG. 5.

FIGS. 4 and 7 illustrate an exemplary gear subassembly 72 for use with the instant invention. The illustrated gear subassembly 72 includes a gear drive 110 that engages a gear 112 that operably engages a lead nut 114, which is in operable engagement with the lead screw 70. However, it is foreseen that the gear assembly 72 may have any other useful configuration known in the art. The gear drive 110 may be, but is not limited to, a spur, beveled, skewed, helical, hydroploid, double helical or crown gear drive. Similarly, the gear 112 is complementary to and cooperates with the gear drive 110, and may have any useful configuration known in the art, such as but not limited to a spur, beveled, skewed, helical, hydroploid, double helical and crown gears. As shown in FIG. 7, the lead nut 114 is operably engaged by or attached to the gear 112. The lead nut 114 includes a thread (not shown) that is operably complementary to the thread of the lead screw 70. For example, if the lead screw 70 is an ACME screw, then the lead nut 114 is an ACME nut. Alternative screw and nut thread configurations are foreseen.

The drive gear 110 includes a gear engagement portion 116 that is associated with the housing access portion 106. The actuator 26, such as but not limited to an external motor, operably connects with the gear engagement portion 116, so as to actuate, power or drive the gear subassembly 72. In some embodiments, the actuator 26 connects, or plugs, directly to the drive gear 110. In other embodiments, the actuator 26 connects indirectly to the gear engagement portion 116 such as but not limited to by a cord that can be plugged thereinto. Numerous alternative configurations known in the art are foreseen.

Upon actuation by the actuator 26, the gear subassembly 72 engages the lead screw 70 by rotating the lead nut 114 in a clockwise or a counter clockwise direction, so as to rotatingly move the lead nut 114 along the length of the lead screw 70, such that, depending upon the direction of lead nut 114 rotation, the carrier member 74 is moved in a direction selected from toward and away from the first brace member 66, thereby lowering and raising the associated end of an attached transfer table 20. For example, the gear drive rotates, causing the rotatingly engaged gear to rotate, such as clockwise or counter clockwise, which in turn causes the lead nut 114 to rotate with respect to the lead screw 70. As is known in the art, such rotation causes the lead nut 114 to rotatingly move up and down the lead screw 70, depending upon the direction of lead nut rotation 114 (e.g., clockwise or counter clockwise).

Referring now to FIGS. 1 and 8-13, the patient positioning apparatus 1 of the present invention is useful for transferring a patient 2 to a patient support structure 4, or surgical table, in a prone position. If the patient 2 is already on the patient support structure 4, the patient positioning apparatus 1 is useful for turning the patient 2 over from a prone position to a supine position, and vice vera.

Referring to FIG. 9, prior to moving the patient 2, the head-end lift subassembly 22 is attached, or installed, to the head-end elevator subassembly 8, and the foot-end lift subassembly 24 is attached, or installed, to the foot-end elevator subassembly 10. These attachments are accomplished by engaging the connection portions 84 of the respective first brace members 66 with the attachment brackets 85 of the respective head-end and foot-end elevator subassemblies 8, 10, using quick release pins 52' to maintain said engagements. These engagements are fixed, such that substantially no hingeable pivoting occurs between the engaged attachment brackets 85 and elevator subassemblies 8, 10.

Figure 10:
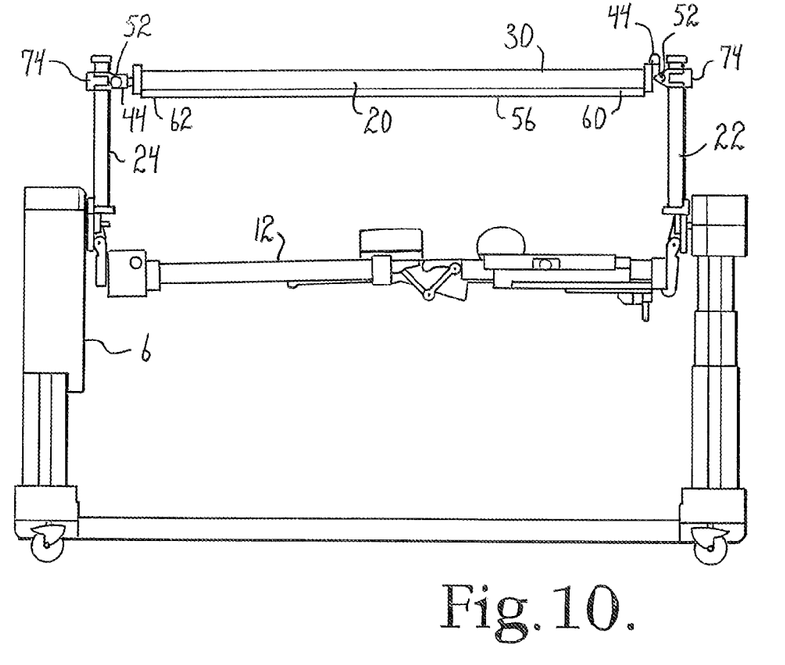
FIG. 10 is a side view of the patient support structure of FIG. 9, with a patient transfer table attached to the head-end and foot-end lift subassemblies, wherein the patient transfer table is spaced a maximum distance from the patient support structure.

Next, as shown in FIG. 10, the transfer table 20 is attached, or installed, to the head-end and foot-end lift subassemblies 20, 24. This is accomplished by hingeably attaching the linkage brackets 44 of the head end cross-beam 38 to the head-end engagement bracket of the head-end lift subassembly 22; and also hingeably attaching the linkage brackets 44 of the foot end cross-beam 38 to the foot-end engagement bracket of the head-end lift subassembly 24. For example, the horizontal channels 45 of linkage brackets 44 are axially aligned with the engagement bracket horizontal through-bores 51, followed by removable insertion of a quick release pin 52 through each aligned horizontal channel 44 and horizontal through-bore 51 pair.

Figure 11:
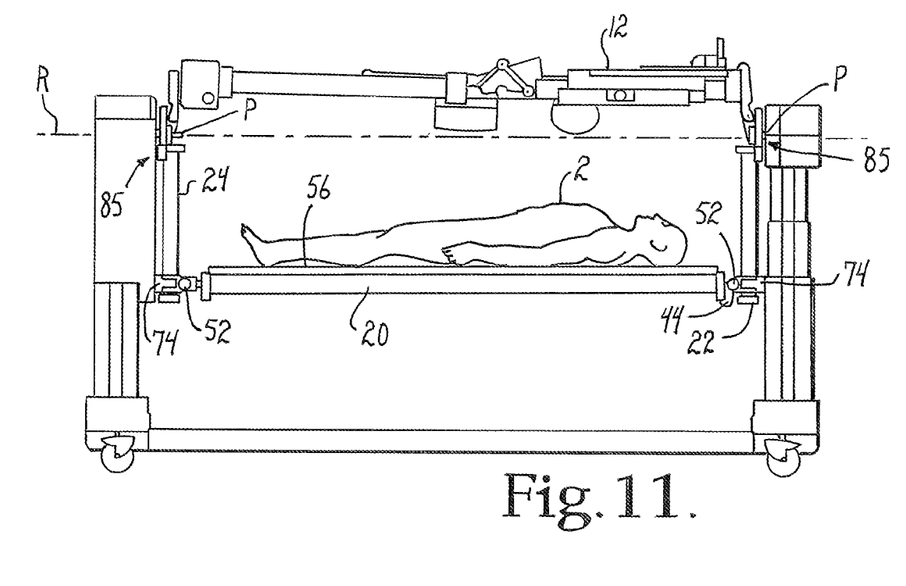
FIG. 11 is a side view of the patient support structure of FIG. 10, wherein the frame of the patient support structure, and the attached patient positioning apparatus, have been rotated about 180° with respect to a longitudinal roll axis, which is denoted by the letter R, and with a patient positioned in a supine position on the patient transfer table.

As shown in FIG. 11, the patient support frame 12 is then rotated, or rolled, about ±180° about the roll axis R, until the transfer table 20 is located below the patient support frame 12. The patient 2 can then be moved to the transfer table 20 from an adjacent bed or gurney, such that the transfer table 20 supports the weight of the patient 2. Generally, the patient 2 is in a supine position, or facing upward, on both the bed and the transfer table 20.

Figure 12:
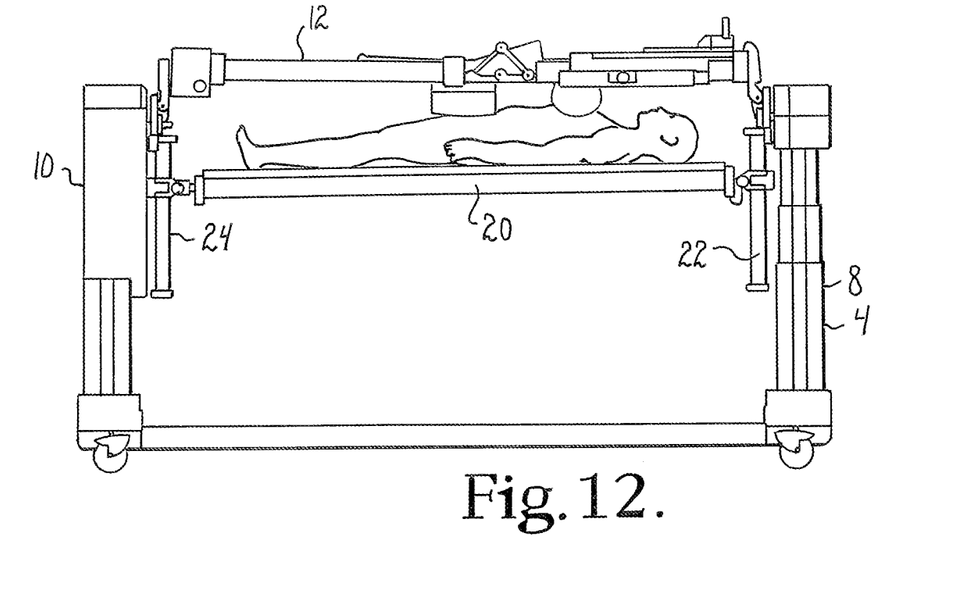
FIG. 12 is a side view of the patient support structure of FIG. 11, wherein the head-end and foot-end lift subassemblies have been synchronously actuated to raise the patient transfer table and the patient toward the frame of the patient support structure, until the patient is pressed against the frame.

Next, as shown in FIG. 12, the patient 2 is lifted by the lift subassemblies 22, 24, until the patient 2 is firmly sandwiched between the transfer table 20 and the patient support frame 12. Specifically, lifting the patient 2 is accomplished by simultaneously actuating the two gear subassemblies 72, so as to move both the head and foot ends 30, 32 of the transfer table 20 toward the rotation axis R at substantially the same rate. In FIG. 12, movement of the transfer table 20 toward the rotation axis R appears as movement away from the floor (not shown) that supports the patient support structure 4. In some embodiments, an external actuator 26, or motor, is releasably attached to each of the gear engagement portions 116, and then the lift subassemblies 22, 24 are actuated simultaneously. During actuation, the lead nuts 114 rotate with respect to the engaged lead screws 70, which in turn causes the attached carrier members 74 to move with respect to the support members 64, thereby simultaneously moving the head and foot ends 30, 32 of the attached transfer table 20. In some embodiments, the gear subassemblies 72 each include an internal actuator 26. For example, an internal actuator 26 may be housed in each of the carrier members 74. In yet another embodiment, the gear subassemblies 72 are actuated by one or more actuators located in the patient support structure 4.

Figure 13:
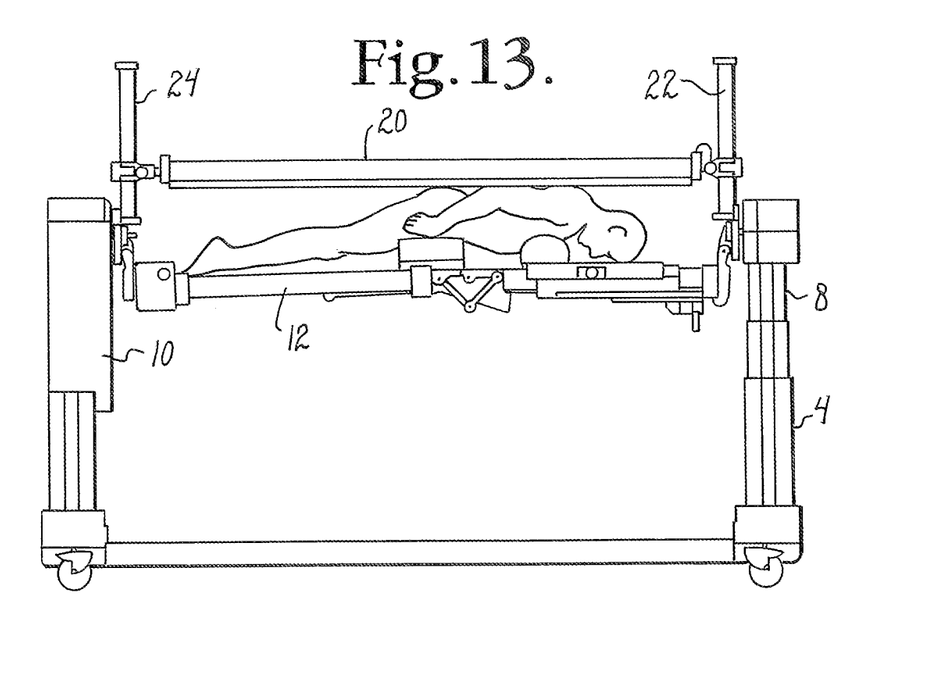
FIG. 13 is a side view of the patient support structure of FIG. 10, wherein the frame and patient positioning apparatus have been rotated back to the starting position, such that the patient rests on the frame in a prone position.

Referring now to FIG. 13, when the patient 2 is sandwiched firmly between the transfer table 20 and the patient support frame 12, the patient support frame 12 is again rotated, or rolled, approximately ±180° with respect to, or about, the roll axis R, such as, for example, until the patient support frame 12 is located below the transfer table 20. During this second rotation, the weight of the patient 2 is transferred from the transfer table 20 to the patient support frame 12. When this second rotation is completed, the patient 2 is in a prone, or downwardly facing, position on the patient support frame 12.

Once the patient 2 is supported by the patient support frame 12 of the patient support structure 4, the patient positioning apparatus 1 may be removed from the patient support structure 4. Such removal is performed by reversing the installation steps described above. For example, the transfer table 20 is lifted a distance above the patient 2 by reversing the actuator 26 and rotating the lead nut 114 with respect to the lead screw 70, such that the patient 2 is no longer sandwiched between the transfer table 20 and the patient support frame 12. Then the quick release pins 52 are removed, and the transfer table 20 is removed from the lift subassemblies 22, 24. And then the lift subassemblies 22, 24 are removed from the respective elevator subassemblies 8, 10 by disconnection, or removal, of the quick release pins 52'.

In some circumstances, it is desirable to turn a patient 2 over, from a prone position to a supine position, while the patient 2 is supported on the patient support frame 4, such as is shown in FIG. 8. Similar to the procedure described above, the head-end and foot-end lift subassemblies 22, 24 are attached to the respective head-end and foot-end elevator subassemblies 8, 10. The apparatus 1 will appear similar to that shown in FIG. 9, with a patient 2 (not shown) in a prone position on the patient support frame 12. Then, the transfer table 20 is attached to the head-end and foot-end lift subassemblies 22, 24. The apparatus 1 will appear similar to what is shown in FIGS. 10 and 13, with a patient 2 (not shown) in a prone position on the patient support frame 12. The transfer table 20 will then be lowered until the patient 2 is firmly sandwiched between the transfer table 20 and the patient support frame 4. In certain embodiments, an imaging table is used instead of a transfer table 20, such that a radiological image of the patient can be taken at this point, or the patient 2 can be rotated over onto the imaging table for such an image. When the patient 2 is firmly sandwiched between the patient support frame 4 and the transfer table 20, or an imaging table, the patient support frame 12 is rotated, or rolled, about ±180° with respect to the roll axis R, such as until the patient support frame 12 is located above the transfer table 20, such as is shown in FIG. 12. The transfer table 20 can then be lowered, such that a radiological image of the patient can be taken or a surgical procedure can be performed on the patient 2 in a supine position, or the patient 2 can be transferred back to a bed or gurney.

It is to be understood that while certain forms of the present invention have been illustrated and described herein, it is not to be limited to the specific forms or arrangement of parts described and shown.

What is claimed and desired to be secured by Letters Patent is as follows:

1. A lifting subassembly for a patient positioning apparatus having a base and a patient support structure, comprising:
    a) a lifting subassembly reversibly attachable to the base and having first and second lifting positions with respect to the base, wherein:
    b) the lifting subassembly is adapted to move the patient support structure from the first lifting position to the second lifting position in a vertical direction above a floor; and
    c) the lifting subassembly is reversibly rotatably from the first lifting position to the second lifting position with respect to the base.

2. The lifting subassembly according to claim 1, wherein the lifting subassembly is removable when in the second lifting position.

3. The lifting subassembly according to claim 1, wherein the lifting subassembly comprises:
    a) a pair of spaced parallel elongate support members, each elongate support member having first and second ends;
    b) spaced parallel first and second brace members, the first brace member joining the first ends of the elongate support members and the second brace member joining the second ends of the elongate support members, so as to provide a frame structure; and
    c) a carrier member located between the brace members and reversibly movable along a length of the elongate support members, whereby the patient support structure is slidingly moved between the first and second lifting positions.

4. The lifting subassembly according to claim 3, further comprising
    a lifting mechanism adapted to move the carrier member.

5. The lifting subassembly according to claim 4, wherein the lifting mechanisms includes:
    a) a lead screw spaced from and parallel with the support members and joined with the brace members; and
    b) a gear subassembly engaging the lead screw so as to move the carrier member along the length of the support members.

6. The lifting subassembly according to claim 3, wherein the carrier member includes at least one engagement member adapted for reversibly engaging the patient support structure.

7. The lifting subassembly according to claim 3, wherein the carrier member includes a pair of spaced parallel ring members, each ring member including a through-bore slidingly receiving one of the elongate support members therethrough, whereby the carrier member is movable between the brace members.

8. The lifting subassembly according to claim 3, wherein at least one of the brace members includes a connection portion adapted for reversible engagement of the base structure.

9. The lifting subassembly according to claim 1, wherein the lifting subassembly comprises a pair of lifting subassemblies.

10. The lifting subassembly according to claim 1, further comprising
    an actuator.

11. A patient positioning apparatus for positioning a patient on a patient support structure for a medical procedure, the patient support structure having a base supporting a removably attachable patient support frame above a floor and a rotation mechanism for rotating the patient support frame about a longitudinally extending roll axis and between first and second lifting positions with respect to the floor, the patient positioning apparatus comprising:
    a) a lifting subassembly reversibly attachable to the base and having a connection portion slidingly movable between the first and second lifting positions with respect to a length of the lifting subassembly; and
    b) a transfer table sized and shaped for receiving and supporting a patient thereon and reversibly attachable to the lifting subassembly.

12. The apparatus according to claim 11, further comprising
    an actuator for actuating the lifting subassembly, so as to move the transfer table between the first and second lifting positions.

13. The apparatus according to claim 11, wherein
    the transfer table includes a bracket for reversible attachment to the lifting subassembly.

14. The apparatus according to claim 11, wherein
    the transfer table includes radio-transparent tabletop member.

15. The apparatus according to claim 11, wherein
    the lifting subassembly includes first and second lifting subassemblies.

16. The apparatus according to claim 15, wherein
    the first and second lifting subassemblies are independently movable.

17. The apparatus according to claim 15, each of the lift subassemblies comprising:
    a) a pair of spaced apart and substantially parallel support members;
    b) a lead screw spaced from and substantially parallel with the support members;
    c) a first brace member joining a first end of each of the support members and the lead screw, the first brace member including an attachment structure for removable attachment to a respective vertical support subassembly;
    d) a second brace member joining a second end of each of the support members and the jack screw; and
    e) a carrier member slidably engaging the support members, the carrier member having
        i) a gear subassembly operably engaging the lead screw so as to reversibly move the carrier member toward the first brace member, and
        ii) a bracket for releasable hingeable attachment to the transfer table.

18. The apparatus according to claim 17, the gear subassembly comprising:
    a) a lead nut rotatably engaging the lead screw; and
    b) a motor connector for operable engagement of an external motor.

19. The apparatus according to claim 17, the carrier member including:
    a) a pair of sliding brackets, each sliding bracket being sized and shaped to slidably engage a support member.

20. The apparatus according to claim 15, further comprising an actuator adapted to synchronously actuate the first and second lifting subassemblies, so as to maintain the transfer table in a plane substantially parallel to the roll axis while moving the transfer table between the first and second lifting positions.

21. The apparatus according to claim 20, wherein
one of the first and second lifting positions is closer to the patient support structure than the other of the first and second lifting positions.

22. The apparatus according to claim 21, wherein
when in the closer of the first and second lifting positions, a patient on the transfer table is substantially sandwiched between the transfer table and the patient support structure.

23. A method of transferring a patient to a medical patient support structure in a prone position, the patient support structure including a base with spaced head-end and foot-end vertical support subassemblies, a patient support frame removably attached to and supported by the vertical support subassemblies, and a rotation mechanism for rotating the patient support frame about a longitudinally extending roll axis a distance of up to at least about ±180°, the method comprising:
 a) providing a patient positioning apparatus having head-end and foot-end lift subassemblies and a transfer table;
 b) releasably attaching the patient positioning apparatus to the patient support structure;
 c) orienting the patient positioning apparatus for patient transfer;
 d) placing a patient on the transfer table in a supine position;
 e) actuating the head-end and foot-end lift subassemblies so as to move the patient toward the patient support frame, such that the patient is snugly sandwiched between the transfer table and the patient support frame;
 f) rotating the patient support structure to a first position, such that the patient supported by the patient support frame in a prone position; and
 g) detaching the patient positioning apparatus from the patient support structure.

24. The method according to claim 23, wherein releasably attaching the patient positioning apparatus to the patient support structure comprises:
 a) attaching the head-end lift subassembly to the head-end vertical support subassembly;
 b) attaching the foot-end lift subassembly to both the foot-end vertical support subassembly; and
 c) attaching the transfer table to the head end and foot-end lift subassemblies.

25. The method according to claim 23, wherein orienting the patient positioning apparatus for patient transfer comprises
rotating the patient support structure from the first position about ±180° about the roll axis such that the transfer table is located below the patient support frame.

26. The method according to claim 23, wherein actuating the head-end and foot-end lift subassemblies comprises
actuating a gear subassembly so as to rotate a lead nut relative to a lead screw.

* * * * *